(12) United States Patent
Kundu et al.

(10) Patent No.: US 7,332,629 B2
(45) Date of Patent: Feb. 19, 2008

(54) MODULATORS (INHIBITORS/ACTIVATORS) OF HISTONE ACETYLTRANSFERASES

(75) Inventors: Tapas Kumar Kundu, Karnataka (IN); Karanam Balasubramanyam, Ellicot City, MD (US); Vankatesh Swaminathan, Kansas City, MO (US)

(73) Assignee: Jawaharlal Nehru Centre for Advanced Scientific Research (IN)

( * ) Notice: Subject to any disclaimer, the term of this patent is extended or adjusted under 35 U.S.C. 154(b) by 0 days.

(21) Appl. No.: 10/538,328

(22) PCT Filed: Dec. 12, 2003

(86) PCT No.: PCT/IN03/00389

§ 371 (c)(1),
(2), (4) Date: Dec. 23, 2005

(87) PCT Pub. No.: WO2004/053140

PCT Pub. Date: Jun. 24, 2004

(65) Prior Publication Data

US 2006/0167107 A1    Jul. 27, 2006

(30) Foreign Application Priority Data

Dec. 12, 2002  (IN) ................ 925/MAS/2002

(51) Int. Cl.
*C07C 233/65*    (2006.01)
*A61K 31/165*    (2006.01)
(52) U.S. Cl. .............. 564/176; 564/177; 514/617; 558/415
(58) Field of Classification Search ............... 564/176, 564/177; 514/617, 520; 558/415
See application file for complete search history.

(56) References Cited

U.S. PATENT DOCUMENTS 3,113,067 A * 12/1963  Strufe et al. ............... 514/166
6,369,030 B1   4/2002  Cole et al.

FOREIGN PATENT DOCUMENTS

JP        02 306916 A2    12/1990
JP        2001 139550 A2   5/2001
WO        WO 2003 103655 A1  12/2003

OTHER PUBLICATIONS

Golub et al, Science, vol. 286, 1999, pp. 531-537.*
Huff, J. Med. Chem, 34(8), 2305-2314.*
Lenz, J. Org. Chem., vol. 39, No. 19, 1974, 2839-2845.*
Humm et al, Arch. Pharm., 321, 419-422, 1988.*
Humm, Alfred W., et al., (1988), "Development of potential nonsteroidal antiandrogens: N-[4-nitro-3-(triflouromethyl)phenyl]cyclohexanecarboxamides and—benzamides and N-(3,4-dichlorophenyl)- and N-(3,4,5-trichlorophenyl)benzamides", Archiv der Pharmazie (Weinheim, Germany), (1988), 321(7), 419-22 (abstract).
Waisser, K., et al., (2001), "Synthesis and antimycobacterial activity of salicylanilides substituted in position 5", Chemical Papers (2001), 55(2), 121-129 (abstract).

* cited by examiner

*Primary Examiner*—Shailendra Kumar
(74) *Attorney, Agent, or Firm*—Joseph T. Leone, Esq.; DeWitt Ross & Stevens S.C.

(57) ABSTRACT

Disclosed are compounds of the formulae:

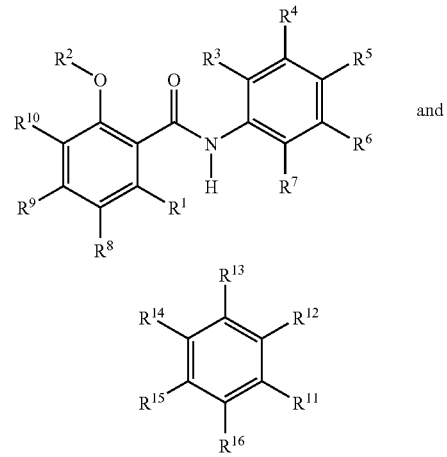

and method of using the compounds to treat cancer, AIDS, HIV infection, and asthma.

5 Claims, 6 Drawing Sheets

FIGURE-1

Formula I

Formula II

MODULATORS (INHIBITORS/ACTIVATORS) OF HISTONE ACETYLTRANSFERASES

CROSS-REFERENCE TO RELATED APPLICATIONS

Priority is hereby claimed to Patent Cooperation Treaty application Serial No. PCT/IN2003/000389, filed Dec. 12, 2003, which claims priority to Indian patent application Serial No. 925/MAS/2002, the entire contents of both of which are incorporated herein.

FIELD OF INVENTION

This invention relates to the field of novel anticancer agents for therapeutic application in human medicine.

BACKGROUND

The eukaryotic genome is organized as a highly complex nucleoprotein structure called chromatin, the unit of which is the nucleosome. The nucleosome is composed of two copies each of four different histones, H3, H2B, H2A, and H4, constituting a scaffold, which is wrapped around by 146 base pairs of DNA. Therefore, for any process that requires access to the DNA (e.g. transcription, replication, recombination, and repair), the chromatin needs to be opened by the remodeling systems. There are two different biochemical processes to modify chromatin structure, namely the covalent modifications of histone tails and the ATP-dependent chromatin remodeling. Among the several covalent modifications of histones known, the reversible acetylation of key lysine residues in histones holds a pivotal position in transcriptional regulation. Acetylation of histones is a distinctive feature of the transcriptionally active genes, whereas deacetylation indicates the repressed state of a gene,. A balance between the acetylation and deacetylation states of histones regulates transcription. Dysfunction of the enzymes involved in these events, the histone acetyltransferases (HATs) and histone deacetylases (HDACs), is often associated with the manifestation of cancer. These enzymes thus become potential new targets for antineoplastic therapy.

A wide repertoire of transcriptional co-activator proteins is now recognized to possess histone acetyltransferase activity. These include p300/CBP-associated factor (PCAF), which is similar to GCN5, nuclear hormone receptor cofactors such as steroid receptor cofactor 1 (SRC1) and activator of thyroid and retinoid receptor (ACTR) and the multifunctional p300/CBP. The p300/CBP is a global transcriptional coactivator, which plays a critical role in a variety of cellular process including cell cycle control, differentiation, and apoptosis. Mutations in p300/CBP are associated with different human cancers and other human diseases. It is one of the most potent histone acetyltransferases, which can acetylate all four-core histones within nucleosomes as well as free histone forms. The HAT activity of p300 is regulated by several other factors. For example, the viral oncoprotein E1A binds to p300 and inhibits its activity, whereas phosphorylation of CBP by cyclin E/Cdk2 kinase activates its HAT activity. During the process of transcription, p300 is recruited on to the chromatin template through the direct interaction with the activator and enhances the transcription by acetylation of promoter proximal nucleosomal histones.

Although significant progress has been made in the field of histone deacetylase inhibitors as antineoplastic therapeutics, and some of the compounds are already in human trials the reports of HAT inhibitors/activators are scanty. Prior to the molecular characterization of HAT enzymes, several polyamine-CoA conjugates were found to block HAT activity in cell extracts. However, the target enzyme(s) for these conjugates was not known. Recently, two peptide-CoA conjugates, namely Lysyl CoA (Lys-CoA) and H3-CoA-20, were synthesized that specifically inhibit the HAT activity of p300 and PCAF, respectively. Thus, there is an urgent medical need to identify new drugs having modulating activity(inhibitors/activators) towards histone acetyltransferases which can be used to treat diseases in which histone acetyltransferase play an important role treatment of diseases due to defects in gene regulation predominantly cancer.

In accordance with the present invention, there is therefore provided the use of a compound of general formula I for activator molecules of histone acetyltransferases and the use of a compound of general formula II for inhibitor molecules of histone acetyltransferases.

DESCRIPTION OF THE INVENTION

Cashew nut shell liquid (CNSL) possessed inhibitory activity towards p300. The systematic bio-activity guided fractionation of CNSL yielded unsaturated anacardic acids mixture, namely, the 8'Z-monoene, the 8'Z, 11'Z-diene, and the 8'Z, 11'Z, 14'Z-triene, which are the chief constituents (~75%) of cashew nutshell liquid (18), having maximum HAT inhibitory activity. The hydrogenation of unsaturated anacardic acids mixture yielded a single compound, Anacardic acid (2-hydroxy-6-pentadecylbenzoic acid) showing an equally potent inhibitory activity towards p300. This data indicated that absence of unsaturation in anacardic acid did not alter its HAT inhibitory property. Neither salicylic acid nor benzoic acid shown any inhnbitory activity against histone acetyltransferases.

Figure 2:
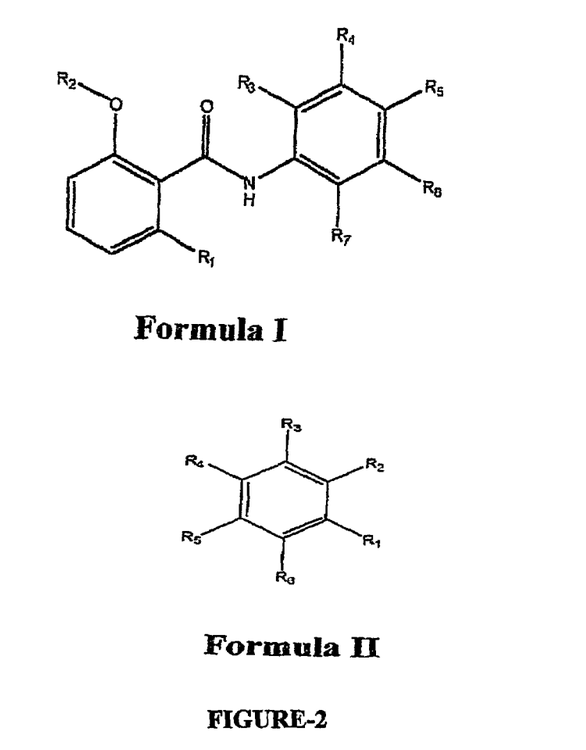
FIG. 2. General formulae of the compounds claimed for the patent.

The rate of the acetylation reaction at different concentrations of the inhibitors (and in its absence) was recorded with increasing concentrations of [$^3$H]-acetyl CoA and a constant amount of core histones. The double reciprocal plot for each inhibitor concentration and in its absence (1/c.p.m vs. 1/[Acetyl CoA]) was plotted as shown in FIG. 2E. The results suggest that anacardic acid is a non-competitive type of p300-HAT inhibitor.

Figure 1:
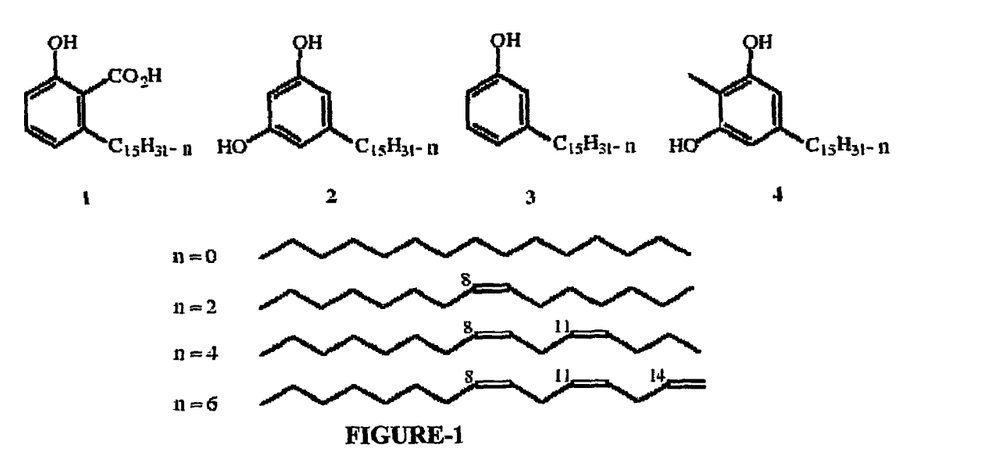
FIG. 1. Different unsaturated anacardic acids present in CNSL.

The acidic group on the both salicylic acid and anacardic acid was modified to respective different amide derivatives using substituted anilides. Most of these compounds, with different anilide moieties on anacardic acid and salicylic acid, when tested in vitro HAT assay (filter binding), surprisingly showed an enhancement in the p300 HAT activity, while keeping the PCAF HAT activity mostly unperturbed. The interchanging of substitution pattern on the ring B in formula I was found to be affecting activation profile of molecule.

Deacetylation of the core histones in the presence or absence of the HAT activating compounds, at 100 µM or 500 µM, shows no difference in the deacetylase enzyme activity indicating no affect on deacetylation activity and the HAT enzyme specificity.

The addition of increasing concentration of either inhibitors or activators does not produce any variation in the transcript levels as compared to the DMSO control indicating that the compounds do not affect any component of the basal transcription machinery.

The template pG$_5$ML-array (8) was assembled into chromatin using the NAP1 mediated assembly method (Experimental Procedures). Addition of activators to the HAT-dependent transcription reaction along with the p300 and acetyl CoA after allowing for 30 min of acetylation either in the presence or absence of the compound. Under these conditions we found the addition of DMSO produced a slight drop in the transcript levels while the addition of activators enhanced the levels of transcription 1.6 fold over the DMSO control. Thus this result indicates that CTPB specifically enhances the HAT activity of p300, a function that is reflected even at the transcriptional level. In order to explain the 1.6-fold increase in transcription levels, in contrast to the ~5-fold increase in the histone acetylation levels; Inhibitors did not affect the transcription from the DNA template, but the HAT-dependent transcription from chromatin template was inhibited by addition of inhibitors at 10 μM concentration.

METHODS

A: Chemical Methods

The cashew nut shell liquid (CNSL) is also known as cashew nut shell oil. CNSL is a dark brown viscous liquid reported to be 15-20% by weight of the unshelled nut in Africa, 25-30% by weight in India and ca. 25% overall. CNSL contains 90% anacardic acid and 10% cardol.

Methods reported to extract CNSL from cashew shells are:

1. Roasting nuts and collecting expelled liquid (Indian native method, yield 50%).
2. Extract with hot CNSL without charring the kernels (yield 85-90%).
3. Super heated steam treatment and collect condensate (used to improve yields of 2).
4. Solvent extraction with hexane leading to more percentage of anacardic acid.
5. Supercritical fluid extraction.

CNSL can also be extracted from cashew nuts that are soaked in water or humidified in piles and then held in a humid atmosphere so that the shell has set moisture content from 15-45% depending on the methods. CNSL is used in the manufacture of brake linings, industrial belting and clutches, reinforcing synthetic rubber, for oil and acid resistance, in lacquers, in electrical insulation material, as a metal anti-corrosive material, for waterproofing and as an adhesive. The use of CNSL in varnishes, lacquers, paints and brake linings requires distillation and further refinement.

Anacardic acid (6-pentadecylsalicylic acid), a major component of cashew nut shell liquid (CNSL), is obtained by solvent extraction of cashew nut shells. It exists as a heterogeneous mixture of monoenes, dienes, and trienes. More specifically Cold processed CNSL was purchased from commercial source. The Anacardic acid present in the CNSL was purified as calcium anacardate by adding Calcium hydroxide to CNSL dissolved in isopropyl alcohol. The pure calcium salt of anacardic acid was dried and treated with IN HCl to release free anacardic acid ene mixture (containing n=0,2,4,6) (General food corporation (Rye, N.Y.) Indian patent, 34671,1946). The ene mixture obtained by above method was hydrogenated in ethylacetate for 4 hrs over 10% palladium-carbon using a Parr hydrogenator. The catalyst was filtered off and the solvent evaporated in vacuo to yield saturated anacardic acid. The alkylation with dimethyl and diethyl sulphates using potassium carbonate gave the dialkylated derivative. Di isopropyl anacardic acid was obtained by using isopropyl bromide in presence of $K_2CO_3$ with phase transfer catalyst in M1BK for 36 hrs.

Dialkylated anacardic acids were treated with potassium tertiary butoxide in DMSO to yield respective O-alkyl anacardic acids. The O-alkyl anacardic acids on treatment with thionyl chloride in the presence of a catalytic amount of DMF yield corresponding O-alkyl anacardic acid chlorides. The resultant acid chlorides condensed with different substituted anilines yielded respective benzamide derivatives.

All compounds were characterized by using FABMS. TLC was done using precoated silica gel $GF_{254}$ plates (Merck, Darmstadt, Germany) with hexane:Ethyl acetate (7:3) as the developing solvent and visualized after spraying with vanillin sulphuric acid reagent.

The following are preparation of starting materials used for synthesis of activator molecules and inhibitor molecules.

Isolation of Anacardic Acid from CNSL. Commercially available solvent-extracted CNSL (1 Kg) was dissolved in 5% aqueous methanol (6.2 L), and calcium hydroxide (510 g) was added in portions under stirring. After complete addition of calcium hydroxide, the temperature of the reaction mixture was raised to 54° C. and stirring was continued for 4 h. The supernatant solution was monitored by TLC for the absence of anacardic acid. After completion of the reaction, the precipitated calcium anacardate was filtered and washed thoroughly with methanol (2.5L), and the cake was dried under vacuum at 45-54° C. for 3 h (dry weight 1.08 Kg). The filtrate was preserved for subsequent isolation of cardol and cardanol. Calcium anacardate (1.08 Kg) was suspended in distilled water (4.5 L) and 11 M HCl (600 mL) was added and stirred for 1.5 h. The resultant solution was extracted with ethyl acetate (2×2 L). The combined organic layer was washed with distilled water (2×2L), dried over anhydrous sodium sulfate, and concentrated under reduced pressure to yield 600 g of mixture of anacardic acid (monoene, diene, and triene).

Preparation of Saturated Anacardic Acid. To a solution of an ene mixture of anacardic acid (500 g, 1300 mmol) in methanol (2.0 L) was added 5% palladium-carbon (25 g), and then hydrogen gas was passed through the solution at 2.5 $kg/cm^2$ until consumption of hydrogen gas ceased (4-5 h). The reaction mass was filtered over a Celite bed and washed with methanol (100 mL). The filtrate was concentrated under reduced pressure to give an off-white solid (477 g), which on recrystallization from hexane yielded 450 g.

Preparation of Methyl 2-methoxy-6-pentadecylbenzoate. To a stirred solution of anacardic acid mentioned above (50 g, 143 mmol) in acetone (300 mL) was added anhydrous powdered potassium carbonate (80 g, 580 mmol). Dimethyl sulfate (44.25 g, 290 mmol) was added in portions for about 10 min at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Methyl 2-methoxy-6-pentadecylbenzoate (45 g, 80%).

Preparation of 2-Methoxy-6-pentadecylbenzoic Acid. To a stirred solution of Methyl 2-methoxy-6-pentadecylbenzoate (10 g, 240 mmol) in dimethyl sulfoxide (40 mL) was added potassium tert-butoxide (10 g, 890 mmol) in portions. The solution was heated to 70° C. on a water bath for 2 h, and the progress of the reaction was monitored by TLC using a hexane-ethyl acetate (8:2) solvent system. The reaction mass was cooled to 10° C., poured into ice water, and then acidified with 5% dilute hydrochloric acid. The precipitated solid was filtered and washed thoroughly with distilled water, and the crude mass was recrystallized in hexane (50 mL) to yield an off-white solid of 2-Methoxy-6-pentadecylbenzoic Acid (7.6 g, 80%).

Preparation of 2-Methoxy-6-pentadecylbenzoyl Chloride. To a stirred solution of 2-Methoxy-6-pentadecylbenzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h After the reaction was complete, the solvent was evaporated under reduced pressure to yield the desired 2-Methoxy-6-pentadecylbenzoyl Chloride, which was redissolved in dichloromethane (50 mL) and used for the condensation with anilides.

Preparation of Ethyl 2-Ethoxy-6-pentadecylbenzoate. To a stirred solution of anacardic acid mentioned above (50 g, 143 mmol) in acetone (300 mL) was added anhydrous powdered potassium carbonate (80 g, 580 mmol). Diethyl sulfate (44.25 g, 290 mmol) was added in portions for about 10 min at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Ethyl 2-Ethoxy-6-pentadecylbenzoate (45 g, 80%).

Preparation of 2-Ethoxy-6-pentadecylbenzoic Acid. To a stirred solution of Ethyl 2-Ethoxy-6-pentadecylbenzoate (20 g, 240 mmol) in dimethyl sulfoxide (80 mL) was added potassium tert-butoxide (20 g, 890 mmol) in portions. The solution was heated to 68° C. on a water bath for 3 h, the reaction was monitored by TLC using a hexane-ethyl acetate (9:1) solvent system. The reaction mass was cooled to 15° C., poured into ice water, and then acidified with 10% dilute hydrochloric acid. The precipitated solid was filtered and washed thoroughly with distilled water, and the crude mass was recrystallized in petroleum ether (50 mL) to yield an off-white solid of 2-Ethoxy-6-pentadecylbenzoic Acid (15 g, 80%).

Preparation of 2-Ethoxy-6-pentadecylbenzoyl Chloride. To a stirred solution of 2-Ethoxy-6-pentadecylbenzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h After the reaction was complete, the solvent was evaporated under reduced pressure to yield the desired 2-Ethoxy-6-pentadecylbenzoyl Chloride, which was redissolved in dichloromethane (50 mL) and used for the condensation with anilides.

Preparation of Propyl 2-propoxy-6-pentadecylbenzoate. To a stirred solution of anacardic acid mentioned above (50 g, 143 mmol) in acetone (300 mL) was added anhydrous powdered potassium carbonate (80 g, 580 mmol). n-propyl iodide (44.25 g 290 mmol) was added in portions for about 24 hrs at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Propyl 2-propoxy-6-pentadecylbenzoate (45 g, 80%).

Preparation of 2-Propoxy-6-pentadecylbenzoic Acid. To a stirred solution of Propyl 2-propoxy-6-pentadecylbenzoate (10 g, 240 mmol) in dimethyl sulfoxide (40 mL) was added potassium tert-butoxide (10 g, 890 mmol) in portions. The solution was heated to 70° C. on a water bath for 2 h, and the progress of the reaction was monitored by TLC using a hexane-ethyl acetate (8:2) solvent system. The reaction mass was cooled to 10° C., poured into ice water, and then acidified with 5% dilute hydrochloric acid. The precipitated solid was filtered and washed thoroughly with distilled water, and the crude mass was recrystallized in hexane (50 mL) to yield an off-white solid of 2-Propoxy-6-pentadecylbenzoic Acid (7.6 g, 80%).

Preparation of 2-Propoxy-6-pentadecylbenzoyl Chloride. To a stirred solution of 2-Ethoxy-6-pentadecylbenzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h. After the reaction was complete, the solvent was evaporated under reduced pressure to yield the desired 2-Propoxy-6-pentadecylbenzoyl Chloride, which was redissolved in dichloromethane (50 mL) and used for the condensation with anilides Preparation of Isopropyl 2-isopropoxy-6-pentadecylbenzoate. To a stirred solution of anacardic acid mentioned above (50 g, 143 mmol) in acetone (300 mL) was added anhydrous powdered potassium carbonate (80 g, 580 mmol). isopropoxyiodide (44.25 g, 290 mmol) was added in portions for about 10 min at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Isopropyl 2-isopropoxy-6-pentadecylbenzoate (45 g, 80%).

Preparation of 2-Isopropoxy-6-pentadecylbenzoic Acid. To a stirred solution of Isopropyl 2-isopropoxy-6-pentadecylbenzoate (10 g, 240 mmol) in dimethyl sulfoxide (40 mL) was added potassium tert-butoxide (10 g, 890 mmol) in portions. The solution was heated to 70° C. on a water bath for 2 h, and the progress of the reaction was monitored by TLC using a hexane-ethyl acetate (8:2) solvent system. The reaction mass was cooled to 10° C., poured into ice water, and then acidified with 5% dilute hydrochloric acid. The precipitated solid was filtered and washed thoroughly with distilled water, and the crude mass was recrystallized in hexane (50 mL) to yield an off-white solid of 2-Isopropoxy-6-pentadecylbenzoic Acid (7.6 g, 80%).

Preparation of 2-Isopropoxy-6-pentadecylbenzoyl Chloride. To a stirred solution of 2-2-Isopropoxy-6-pentadecylbenzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h. After the reaction was complete, the solvent was evaporated under reduced pressure to yield the desired 2-Isopropoxy-6-pentadecylbenzoyl Chloride, which was redissolved in dichloromethane (50 mL) and used for condensation with anilides.

Preparation of Methyl 2-methoxy-benzoate. To a stirred solution of salicylic acid (50 g, 143 mmol) in acetone (300 mL) was added anhydrous powdered potassium carbonate (80 g, 580 mmol). Dimethyl sulfate (44.25 g, 290 mmol) was added in portions for about 10 min at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Methyl 2-methoxy-benzoate (45 g, 80%).

Preparation of 2-Methoxy-benzoic Acid. To a stirred solution of V (10 g, 240 mmol) in dimethyl sulfoxide (40 mL) was added potassium tert-butoxide (10 g, 890 mmol) in portions. The solution was heated to 70° C. on a water bath for 2 h, and the progress of the reaction was monitored by TLC using a hexane-ethyl acetate (8:2) solvent system. The reaction mass was cooled to 10° C., poured into ice water, and then acidified with 5% dilute hydrochloric acid. The precipitated solid was filtered and washed thoroughly with distilled water, and the crude mass was recrystallized in hexane (50 mL) to yield an off-white solid of 2-Methoxy-benzoic Acid (7.6 g, 80%).

Preparation of 2-Methoy-benzoyl Chloride. To a stirred solution of 2-Methoxy-benzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h. After the reaction was complete, the solvent was evaporated under reduced pressure to yield the desired 2-Methoxy-benzoyl Chloride, which was redissolved in dichloromethane (50 mL) and used for the condensation with anilides.

Preparation of Ethyl 2-Ethoxy-benzoate. To a stirred solution of Salicylic acid (50 g, 143 mmol) in acetone (300 mL) was added anhydrous powdered potassium carbonate (80 g, 580 mmol). Diethyl sulfate (44.25 g, 290 mmol) was added in portions for about 10 min at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Ethyl 2-Ethoxy-benzoate (45 g, 80%).

Preparation of 2-Ethoxy-benzoic Acid. To a stirred solution of Ethyl 2-Ethoxy-benzoate (10 g, 240 mmol) in dimethyl sulfoxide (40 mL) was added potassium tert-butoxide (10 g, 890 mmol) in portions. The solution was heated to 70° C. on a water bath for 2 h, and the progress of the reaction was monitored by TLC using a hexane-ethyl acetate (8:2) solvent system. The reaction mass was cooled to 10° C., poured into ice water, and then acidified with 5% dilute hydrochloric acid. The precipitated solid was filtered and washed thoroughly with distilled water, and the crude mass was recrystallized in hexane (50 mL) to yield an off-white solid of 2-Ethoxy-benzoic Acid (7.6 g, 80%).

Preparation of 2-Ethoxy-benzoyl Chloride. To a stirred solution of 2-Ethoxy-6-pentadecylbenzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h. After the reaction was complete, the solvent was evaporated under reduced pressure to yield the desired 2-Ethoxy-benzoyl Chloride, which was redissolved in dichloromethane (50 mL) and used for the condensation with anilides.

Preparation of Propyl 2-propoxy-6-pentadecylbenzoate. To a stirred solution of Salicylic acid mentioned above (50 g, 143 mmol) in ACETONE (300 mL) was added anhydrous powdered potassium carbonate (80 g, 580 mmol). n-propyl iodide (44.25 g, 290 mmol) was added in portions for about 24 hrs at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Propyl 2-propoxy-benzoate (45 g, 80%).

Preparation of 2-Propoxy-benzoic Acid. To a stirred solution of Propyl 2-propoxy-benzoate (10 g, 240 mmol) in dimethyl sulfoxide (40 mL) was added potassium tert-butoxide (10 g, 890 mmol) in portions. The solution was heated to 70° C. on a water bath for 2 h, and the progress of the reaction was monitored by TLC using a hexane-ethyl acetate (8:2) solvent system. The reaction mass was cooled to 10° C., poured into ice water, and then acidified with 5% dilute hydrochloric acid. The precipitated solid was filtered and washed thoroughly with distilled water, and the crude mass was recrystallized in hexane (50 mL) to yield an off-white solid of 2-Propoxy-benzoic Acid (7.6 g, 80%).

Preparation of 2-Propoxy-benzoyl Chloride. To a stirred solution of 2-Propoxy-benzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h. After the reaction was complete, the solvent was evaporated under reduced pressure to yield the desired 2-Propoxy-6-pentadecylbenzoyl Chloride, which was redissolved in dichloromethane (50 mL) and used for the condensation with anilides.

Preparation of Isopropyl 2-isopropoxy-benzoate. To a stirred solution of anacardic acid mentioned above (50 g, 143 mmol) in acetone (300 mL) was added anhydrous powdered potassium carbonate (80 g, 580 mmol). isopropyl iodide (44.25 g, 290 mmol) was added in portions for about 10 min at room temperature. After the addition was complete, the solution was heated to reflux temperature on a water bath and maintained for 3 h. The solution was cooled to room temperature and then concentrated under reduced pressure. Distilled water (200 mL) was added to the reaction mixture, which was then extracted with ethyl acetate (200 mL). The organic layer was washed with distilled water (2×200 mL), dried over anhydrous sodium sulfate, and concentrated to yield the title Isopropyl 2-isopropoxy-benzoate (45 g, 80%).

Preparation of 2-Isopropoxy-benzoic Acid. To a stirred solution of Isopropyl 2-isopropoxy-benzoate (10 g, 240 mmol) in dimethyl sulfoxide (40 mL) was added potassium tert-butoxide (10 g, 890 mmol) in portions. The solution was heated to 70° C. on a water bath for 2 h, and the progress of the reaction was monitored by TLC using a hexane-ethyl acetate (8:2) solvent system. The reaction mass was cooled to 10° C., poured into ice water, and then acidified with 5% dilute hydrochloric acid. The precipitated solid was filtered and washed thoroughly with distilled water, and the crude mass was recrystallized in hexane (50 mL) to yield an off-white solid of 2-Isopropoxy-benzoic Acid (7.6 g, 80%).

Preparation of 2-Isopropoxy-benzoyl Chloride. To a stirred solution of 2-Isopropoxy-benzoic Acid (6.5 g, 16 mmol) in hexane (60 mL) were added thionyl chloride (2.5 g, 21 mmol) and N,N-dimethylformamide (0.5 mL). The reaction mixture was heated to reflux for 1 h. After the reaction was complete, the solvent was evaporated under reduced pressure to yield the desired 2-Isopropoxy-6-pentadecylbenzoyl Chloride, which was redissolved in dichloromethane (50 mL) and used for condensation with following anilides to yield respective benzamides.

B: Biochemical Methods:

Purification of Human Core Histones and Recombinant Proteins—Human core histones were purified from HeLa nuclear pellet as described previously (13). The FLAG epitope tagged Human Topoisomerase I, histone deacetylase 1 (HDAC1) and PCAF, were purified from the recombinant baculovirus infected insect cell line, Sf21, by the immunoaffinity purification using M2-agarose (SIGMA) (14). Full-length p300 was also purified from the recombinant baculovirus infected Sf21 cells as a $His_6$-tagged protein through the Ni-NTA affinity column (Qiagen) as described previously (13). The $His_6$-tagged nucleosome assembly protein 1 (NAP1), used for the in vitro chromatin assembly was purified from E.coli cells as previously reported (13) and the FLAG-tagged chimeric activator Gal4-VP16, expressed in E. coli and purified by immunoaffinity purification with N2 agarose. Human positive transcriptional coactivator, PC4, was expressed in E.coli and purified as described earlier (15).

The peptide substrate, a 45 residue core histone H3 N-terminal peptide (N-CARTKQTARKSTG-GKAPRQLASKAARKSAPSTGGVKKPHRYKPG-C) was synthesized.

HAT Assay: Each of the compounds of Examples 1 to 26 were assessed for inhibition/activation of histone acetyltransferase activity of enzymes p300, PCAF and CBP. HAT assays were performed as described elsewhere (13). Briefly, indicated amounts of proteins/peptide were incubated in HAT-assay buffer containing 50 mM Tris-HCl, pH 8.0, 10% (v/v) glycerol, 1 mM dithiothreitol, 1 mM phenylmethyl sulfonyl fluoride, 0.1 mM EDTA, pH 8.0, 10 mM sodium-butyrate at 30° C. for 10 min in presence or absence of compound followed by the addition of 1 µl of 6.2 Ci/mmol [$^3$H]-acetyl Coenzyme A (acetyl-CoA) and were further incubated for another 10 min. The final reaction volume was 30 µl. The reaction mixture was then blotted onto P-81 (Whatman) filter papers and radioactive counts were recorded on a Wallac 1409 liquid scintillation counter.

In order to characterize the inhibition kinetics of anacardic acid, filter-binding assays were done using constant amount of HeLa core histones in the presence or absence of AA with increasing concentrations of [$^3$H]-acetyl CoA (see Figure Legends, 2E). To visualize the radiolabeled acetylated histones, the reaction mixtures were resolved on 15% SDS-PAGE and processed for fluorography as described elsewhere (15).

Histone deacetylase assay: Deacetylation assays were performed in the HAT assay buffer without sodium butyrate. 2 µg of core histones were incubated with 20 ng of p300 and 1 µl of 6.2 Ci/mmol [$^3$H]-acetyl CoA for 15 min at 30° C. The activity of p300 was inhibited by incubating the reaction mixture with 10 nM p300-HAT specific inhibitor, Lysyl-CoA (10), for 10 min after which 50 ng of HDAC1 was added, in the presence or absence of the compounds, and incubated further for 45 min. The samples were analysed by flourography.

In Vitro Chromadin assembly: Chromatin template for in vitro transcription experiments was assembled and characterized as described earlier (8).

In Vitro Transcription Assay: Transcription assays were essentially carried out as described elsewhere (8), with minor modifications. The scheme of transcription is enumerated in FIG. 5A. Briefly, 30 ng of DNA/equivalent amount of chromatin template was incubated with 30 ng of activator (Gal4-VP16) in a buffer containing 4 mM HEPES (pH 7.8), 20 mM KCl, 2 mM DTT, 0.2 mM PMSF, 10 mM sodium butyrate, 0.1 mg/ml BSA, 2% glycerol (8). The activating compounds were added to the acetylation reaction along with p300 and acetyl-CoA, and incubated for 30 min. at 30° C. This was followed by addition of the p300 specific inhibitor Lysyl CoA (5 µM) to quench the acetylation reaction.

For inhibitors, the HAT p300 was pre-incubated with indicated amounts of inhibitor on ice for 20 min., following which it was added to the acetylation reaction in the transcription assay. For the DNA transcription assays and chromatin transcription inhibition assays, the Lysyl CoA step was omitted. After acetylation, HeLa nuclear extract (5 µl, which contains ~8 mg/ml protein) was added to initiate the pre-initiation complex formation. Transcription reaction was started by the addition of NTP-mix and α-[$^{32}$P]-UTP, after the pre-initiation complex formation. The incubation was continued for 40 min at 30° C. Transcription was terminated by the addition of 250 µl stop buffer (20 mM Tris-HCl pH 8.0, 1 mM EDTA, 100 mM NaCl, 1% SDS and 0.025 ng/µl tRNA). The $^{32}$P-radiolabeled transcript was extracted with phenol-chloroform, ethanol precipitated, dried pellet dissolved in loading dye (8 M Urea, 0.005% bromophenol blue and xylene cyanol) and analyzed on 5% urea-polyacrylamide gel. Gels were then dried and subjected to autoradiography at −70° C. Quantification of transcription was done by Fuji BAS system. Quantitaion of DNA and chromatin transcription data represents three independent experiments.

The following Examples illustrate the preparation of compounds of formula I using the starting materials described above:

EXAMPLE 1

2-Ethoxy-N-(4-nitro-3-trifluromethyl-phenyl)-benzamide 2-ethoxy--benzoyl chloride was condensed with 5-Amino-2-nitrobenzotrifluoride in dichloromethane in presence of triethylamine as acid scavenger to yield 2-Ethoxy-N-(4-nitro-3-trifluromethyl-phenyl)-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:δ6.95-8.10 (7H,aromatic), δ3.98(2H,t,OCH2), δ1.33(3H,t,Methyl)

EXAMPLE 2

2-Methoxy-N-(4-nitro-3-trifluromethyl-phenyl)-benzamide

2-Methoxy-benzoyl chloride was condensed with 5-Amino-2-nitrobenzotrifluoride in dichloromethane in presence of triethylamine as acid scavenger to yield 2-Methoxy-N-(4-nitro-3-trifluromethyl-phenyl)-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:δ6.95-8.10 (7H,aromatic), δ3.73(3H,t,Methyl).

EXAMPLE 3

2-Propoxy-N-(4-nitro-3-trifluromethyl-phenyl)-benzamide

2-Propoxy-benzoyl chloride was condensed with 5-Amino-2-nitrobenzotrifluoride in dichloromethane in presence of triethylamine as acid scavenger to yield 2-Propoxy-N-(4-nitro-3-trifluromethyl-phenyl)-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:δ6.95-8.10 (7H,aromatic), δ3.94(2H,t,OCH2), δ1.75 (2H,t,Methylene) δ0.96 (3H,t,Methyl).

EXAMPLE 4

2-Isopropoxy-N-(4nitro-3-trifluromethyl-phenyl)-benzamide

2-Isopropoxy-benzoyl chloride was condensed with 5-Amino-2-nitrobenzotrifluoride in dichloromethane in presence of triethylamine as acid scavenger to yield 2-Isopropoxy-N-(4-nitro-3-trifluromethyl-phenyl)-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:δ6.95-8.10 (7H,aromatic), δ4.04(1H,m,OCH), δ1.75(2H,t,Methylene) δ1.38 (6H,d,Methyl).

EXAMPLE 5

N-(4-Chloro-3-trifluoromethyl-phenyl)-2-ethoxy-6-pentadecyl-benzamide (CTPB):

2-ethoxy-6-pentadecyl-benzoyl chloride was condensed with 5-amino-2-chloro benzenetrifluoride in dichloromethane in presence of triethylamine as acid scavenger to yield N-(4Chloro-3-trifluoromethyl-phenyl)-2-ethoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo.

The residue obtained was chromatographed over silica gel to afford the desired product.

m/z: 554.6 (M+1),359.6, 175.1, 149.1, 107.1,91,55.1, X-ray data also included

EXAMPLE 6

N-(4-Cyano-3-trifluoromethyl-phenyl)-2-ethoxy-6-pentadecyl-benzamide 2-ethoxy-6-pentadecyl-benzoyl chloride was condensed with 4-Amino-2-trifluromethyl benzonitrile in dichloromethane in presence of triethylamine as acid scavenger to, yield N-(4-Cyano-3-trifluoromethyl-phenyl)-2-ethoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 545.5 (M+1),359.6, 331.6, 213.3, 175.1, 149.1, 107.1,91,55.1

EXAMPLE 7

N-(4-Chloro-3-trifluoromethyl-phenyl)-2-methoxy-6-pentadecyl-benzamide

2-Methoxy-6-pentadecyl-benzoyl chloride was condensed with 5-amino-2-chloro benzenetriflouride in dichloromethane in presence of triethylamine as acid scavenger to yield N-(4-Chloro-3-trifluoromethyl-phenyl)-2-methoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 540.4 (M+1),345.6, 161.1, 149.1, 121.1, 91, 55.1

EXAMPLE 8

N-(4-Cyano-3-trifluoromethyl-phenyl)-2-methoxy-6-pentadecyl-benzamide

2-Methoxy-6-pentadecyl-benzoyl chloride was condensed with 4-Amino-2-trifluromethyl benzonitrile in dichloromethane in presence of triethylamine as acid scavenger to yield N-(4-Cyano-3-trifluoromethyl-phenyl)-2-methoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 531.6 (M+1),345.7, 161, 149.2, 121.1,91,55.1

EXAMPLE 9

N-(4-Chloro-3-trifluoromethyl-phenyl)-2-n-propoxy-6-pentadecyl-benzamide

2-Propoxy-6-pentadecyl-benzoyl chloride was condensed with 5-amino-2-chloro benzenetriflouride in dichloromethane in presence of triethylamine as acid scavenger to yield N-(4-Chloro-3-trifluoromethyl-phenyl)-2-n-propoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z:568.8(M+1),526,373,331,236,147,133,107,83,55

EXAMPLE 10

N-(4-Chloro-3-trifluoromethyl-phenyl)-2-isopropoxy-6-pentadecyl-benzamide

2-Isopropoxy-6-pentadecyl-benzoyl chloride was condensed with 5-amino-2-chloro benzenetriflouride in dichloromethane in presence of triethylamine as acid scavenger to yield N-(4-Chloro-3-trifluoromethyl-phenyl)-2-isopropoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z:568.8(M+1),526,373,331,236,147,133,107,83,55

EXAMPLE 11

N-(4-Cyano-3-trifluoromethyl-phenyl)-2-n-propoxy-6-pentadecyl-benzamide

2-Propoxy-6-pentadecyl-benzoyl chloride was condensed with 4-Amino-2-trifluromethyl benzonitrile in dichloromethane in presence of triethylamine as acid scavenger to yield N-(4-Cyano-3-trifluoromethyl-phenyl)-2-n-propoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 560 (M+1),517,446,373,331,147,107,91

EXAMPLE 12

N-(4-Cyano-3-trifluoromethyl-phenyl)-2-isopropoxy-6-pentadecyl-benzamide

2-Isopropoxy-6-pentadecyl-benzoyl chloride was condensed with 4-Amino-2-trifluromethyl benzonitrile in dichloromethane in presence of triethylamine as acid scavenger to yield N-(4-Cyano-3-trifluoromethyl-phenyl)-2-isopropoxy-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 560 (M+1),517,446,373,331,147,107,91,55.1

EXAMPLE 13

N-(4Chloro-3-trifluoromethyl-phenyl)-2-ethoxy-benzamide (CTB)

2-ethoxy-6-pentadecyl-benzoyl chloride was condensed with 5-amino-2-chloro benzenetriflouride in dichloromethane in presence of triethylamine as acid scavenger to yield N-(4-Chloro-3-trifluoromethyl-phenyl)-2-ethoxy-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 344.4 (M+1),239,149,121,102,82,57

EXAMPLE 14

N-(4Cyano-3-trifluoromethyl-phenyl)-2-ethoxy-benzamide 2-ethoxy-6-pentadecyl-benzoyl chloride was condensed with 4-Amino-2-trifluromethyl benzonitrile in dichloromethane in presence of triethylamine as acid scavenger to yield N-(4-Cyano-3-trifluoromethyl-phenyl)-2-ethoxy-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:$\delta$6.95-8.01 (7H,aromatic), $\delta$3.98(2H,m,OCH2), $\delta$1.33(3H,t,Methyl)

EXAMPLE 15

N-(4Chloro-3-trifluoromethyl-phenyl)-2-methoxy-benzamide

2-Methoxy-6-pentadecyl-benzoyl chloride was condensed with 5-amino-2-chloro benzenetriflouride in dichloromethane in presence of triethylamine as acid scavenger to yield N-(4-Chloro-3-trifluoromethyl-phenyl)-2-methoxy-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:$\delta$6.95-7.40 (7H,aromatic), $\delta$3.73(3H,s,OCH3)

EXAMPLE 16

N-(4-Cyano-3-trifluoromethyl-phenyl)-2-methoxy-benzamide

2-Methoxy-6-pentadecyl-benzoyl chloride was condensed with 4-Amino-2-trifluromethyl benzonitrile in dichloromethane in presence of triethylamine as acid scavenger to yield N-(4-Cyano-3-trifluoromethyl-phenyl)-2-methoxy-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:$\delta$6.95-8.01 (7H,aromatic), $\delta$3.73(3H,OCH3)

EXAMPLE 17

N-(4-Chloro-3-trifluoromethyl-phenyl)-2-n-propoxy-benzamide

2-Propoxy-benzoyl chloride was condensed with 5-amino-2-chloro benzenetriflouride in dichloromethane in presence of triethylamine as acid scavenger to yield N-(4-Chloro-3-trifluoromethyl-phenyl)-2-n-propoxy-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:δ6.95-8.01(7H,aromatic),δ3.94(2H,t,OCH2), δ1.75(2H,m,Methylene), δ0.96(3H,t,Methyl)

EXAMPLE 18

N-(4-Cyano-3-trifluoromethyl-phenyl)-2-Isopropoxy-benzamide

2-Isopropoxy-benzoyl chloride was condensed with 4-Amino-2-trifluromethyl benzonitrile in dichloromethane in presence of triethylamine as acid scavenger to yield N-4-Cyano-3-trifluoromethyl-phenyl)-2-Isopropoxy-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

1H-NMR:δ6.95-8.01 (7H,aromatic), δ4.04(1H,m,OCH), δ1.38(6H,d,Methyl)

EXAMPLE 19

2-Ethoxy-N-(4-nitro-3-trifluromethyl-phenyl)-6-pentadecyl-benzamide 2-ethoxy-6-pentadecyl-benzoyl chloride was condensed with 5-Amino-2-nitrobenzotrifluoride in dichloromethane in presence of triethylamine as acid scavenger to yield 2-Ethoxy-N-(4-nitro-3-trifluromethyl-phenyl)-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 565(because of NO2),359,175,149,136,107,77

EXAMPLE 20

2-Methoxy-N-(4-nitro-3-trifluromethyl-phenyl)-6-pentadecyl-benzamide

2-Methoxy-6-pentadecyl-benzoyl chloride was condensed with 5-Amino-2-nitrobenzotrifluoride in dichloromethane in presence of triethylamine as acid scavenger to yield 2-Methoxy-N-(4-nitro-3-trifluromethyl-phenyl)-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 551(because of NO2),345, 161,149,121,91

EXAMPLE 21

2-Propoxy-N-(4-nitro-3-trifluromethyl-phenyl)-6-pentadecyl-benzamide

2-Propoxy-6-pentadecyl-benzoyl chloride was condensed with 5-Amino-2-nitrobenzotrifluoride in dichloromethane in presence of triethylamine as acid scavenger to yield 2-Propoxy-N-(4-nitro-3-trifluromethyl-phenyl)-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 580(because of NO2),537,373,331,189,161,147,91

EXAMPLE 22

2-Isopropoxy-N-(4-nitro-3-trifluromethyl-phenyl)-6-pentadecyl-benzamide

2-Isopropoxy-6-pentadecyl-benzoyl chloride was condensed with 5-Amino-2-nitrobenzotrifluoride in dichloromethane in presence of triethylamine as acid scavenger to yield 2-Isopropoxy-N-(4-nitro-3-trifluromethyl-phenyl)-6-pentadecyl-benzamide. The reaction mixture was then concentrated in vacuo and the residue was extracted into ethyl acetate. The ethyl acetate layer was washed with water and with cold aqueous hydrochloric acid, then dried over sodium sulphate and finally concentrated in vacuo. The residue obtained was chromatographed over silica gel to afford the desired product.

m/z: 580(because of NO2),537,373,331,189,161,147,107, 91

EXAMPLE 23

Anacardic Acid

Isolation of Anacardic Acid from CNSL. Commercially available solvent-extracted CNSL (1 Kg) was dissolved in 5% aqueous methanol (6.2 L), and calcium hydroxide (510 g) was added in portions under stirring. After complete addition of calcium hydroxide, the temperature of the reaction mixture was raised to 54° C. and stirring was continued for 4 h. The supernatant solution was monitored by TLC for the absence of anacardic acid. After completion of the reaction, the precipitated calcium anacardate was filtered and washed thoroughly with methanol (2.5 L), and the cake was dried under vacuum at 45-54° C. for 3 h (dry weight 1.08 Kg). The filtrate was preserved for subsequent isolation of cardol and cardanol. Calcium anacardate (1.08 Kg) was suspended in distilled water (4.5 L) and 11 M HCl (600 mL) was added and stirred for 1.5 h. The resultant solution was extracted with ethyl acetate (2×2 L). The combined organic layer was washed with distilled water (2×2 L), dried over anhydrous sodium sulfate, and concentrated under reduced pressure to yield 600 g of mixture of anacardic acid (monoene, diene, and triene).

Preparation of Saturated Anacardic Acid. To a solution of an ene mixture of anacardic acid (500 g, 1300 mmol) in methanol (2.0 L) was added 5% palladium-carbon (25 g), and then hydrogen gas was passed through the solution at 2.5 kg/cm² until consumption of hydrogen gas ceased (4-5 h). The reaction mass was filtered over a Celite bed and washed with methanol (100 mL). The filtrate was concentrated under reduced pressure to give an off-white solid (477 g), which on recrystallization from hexane yielded 450 g.

EXAMPLE 24

Anacardic Alcohol

To a stirred solution of Ethyl 2-ethoxy-6-pentadecylbenzoate was reduced to alcohol using lithium aluminum hydride.

m/z: 334.9(M+1)317,163,147,133,121,107,91,69,55

EXAMPLE 25

Anacardic Aldehyde

Anacardic alcohol was oxidized to corresponding anacardic aldehyde using pyridinium chloro chromate.

m/z: 334.9(M+1)317,163,147,133,121,107,91,69,55

EXAMPLE 26

2-Ethoxy-6-pentadecyl-benzoic acid

To a stirred solution of Ethyl 2-Ethoxy-6-pentadecylbenzoate (20 g, 240 mmol) in dimethyl sulfoxide (80 mL) was added potassium tert-butoxide (20 g, 890 mmol) in portions. The solution was heated to 68° C. on a water bath for 3 h, the reaction was monitored by TLC using a hexane-ethyl acetate (9:1) solvent system. The reaction mass was cooled to 15° C., poured into ice water, and then acidified with 10% dilute hydrochloric acid. The precipitated solid was filtered and washed thoroughly with distilled water, and the crude mass was recrystallized in petroleum ether (50 mL) to yield an off-white solid of 2-Ethoxy-6-pentadecylbenzoic Acid (15 g, 80%).

1H-NMR:δ6.80-7.44 (3H,aromatic), δ3.98(2H,m,OCH2), δ2.55(2H,m,Ar-CH2),1.29-1.63 (26H,m,methylene), δ1.33 (3H,t,methyl next to OCH2), δ0.96 (3H,t,Methyl)

EXAMPLE 27

Cardanol:

Commercially available solvent-extracted CNSL (1 Kg) was dissolved in 5% aqueous methanol (6.2 L), and calcium hydroxide (510 g) was added in portions under stirring. After complete addition of calcium hydroxide, the temperature of the reaction mixture was raised to 54° C. and stirring was continued for 4 h. The supernatant solution was monitored by TLC for the absence of anacardic acid. After completion of the reaction, the precipitated calcium anacardate was filtered and washed thoroughly with methanol (2.5 L). The methanol layer was collected and concentrated in vacuo. The concentrate was further purified on silica gel (100-200 mesh) by column chromatography by using increasing amounts ethyl acetate in hexane to fractionate cardanol.

m/z: 304.7(M+1)149,121,107,95,71,57

EXAMPLE 28

Cardol:

Commercially available solvent-extracted CNSL (1 Kg) was dissolved in 5% aqueous methanol (6.2 L), and calcium hydroxide (510 g) was added in portions under stirring. After complete addition of calcium hydroxide, the temperature of the reaction mixture was raised to 54° C. and stirring was continued for 4 h. The supernatant solution was monitored by TLC for the absence of anacardic acid. After completion of the reaction, the precipitated calcium anacardate was filtered and washed thoroughly with methanol (2.5 L). The methanol layer was collected and concentrated in vacuo. The concentrate was further purified on silica gel (100-200 mesh) by column chromatography by using increasing amounts ethyl acetate in hexane to fractionate cardol.

m/z: 321(N+1),149,123,107,95,69,55

Results:

We have identified a small molecule compound, anacardic acid, from Cashew Nut Shell Liquid, know to have anti-tumor activity, which inhibits HAT activity of p300 and PCAF (FIG. 1).

Figure 3:
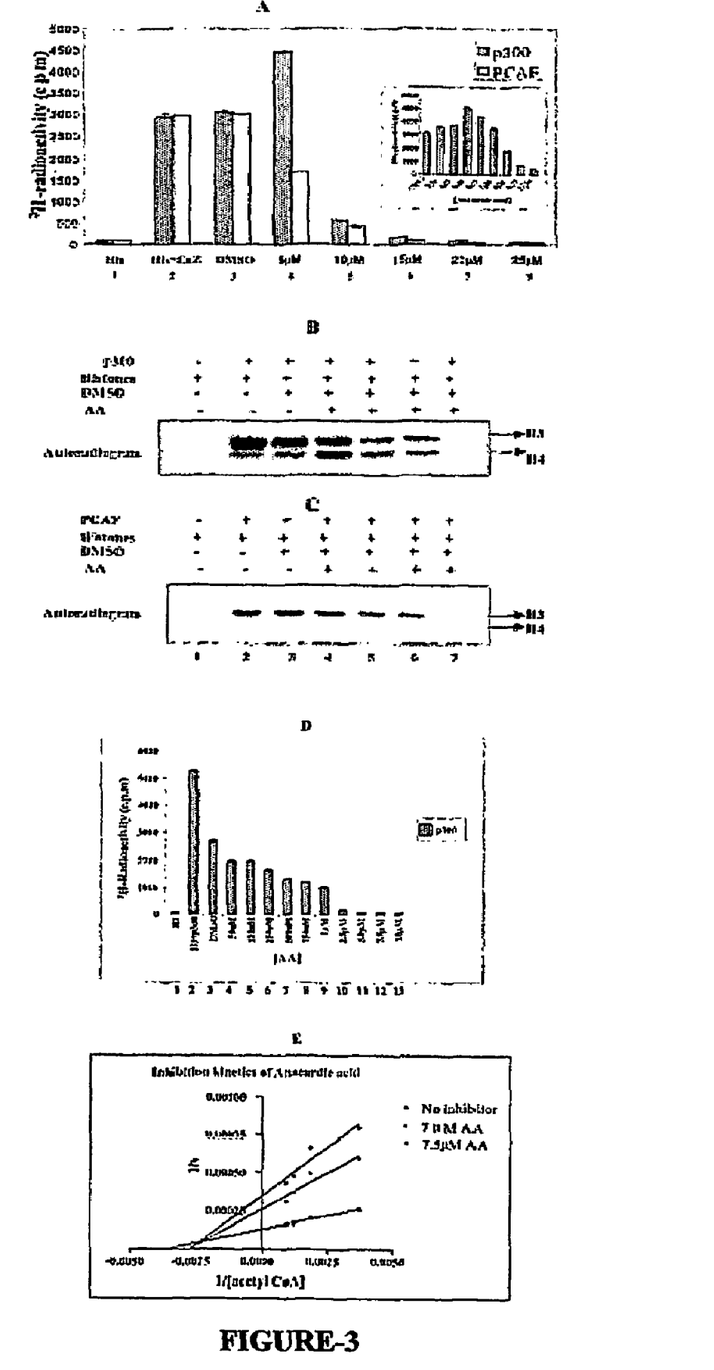
FIG. 3. Effect of increasing concentration of Anacardic acid on the histone acetyltransferase activity of p300 and PCAF.
Figure 4:
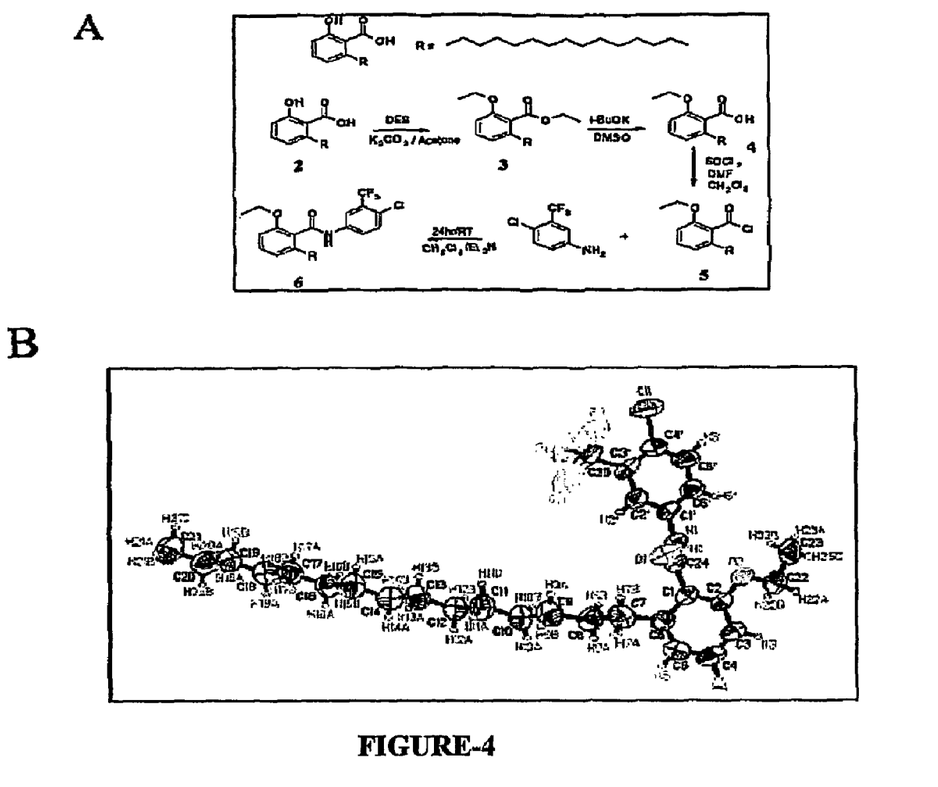
FIG. 4. X-ray crystal structure of N-(4-Chloro-3-trifluoromethyl-phenyl)-2-ethoxy-6-pentadecyl-benzamide (CTPB)
Figure 5:
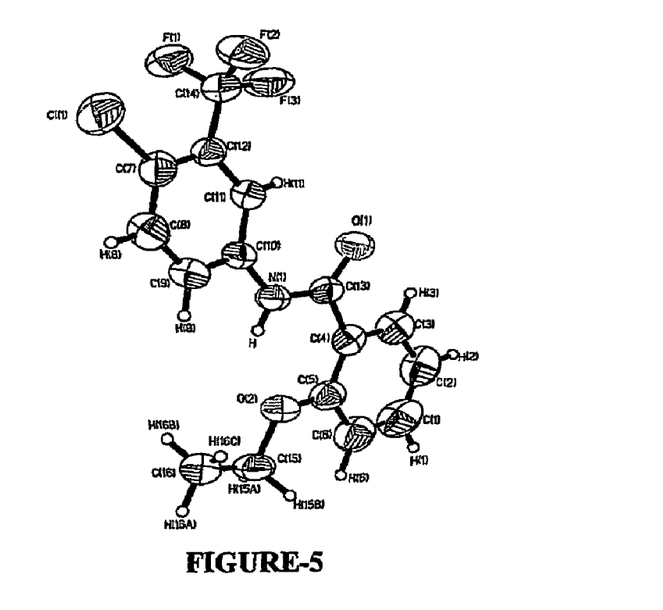
FIG. 5. X-ray crystal structure of N-(4-Chloro-3-trifluoromethyl-phenyl)-2-ethoxy-benzamide (CTPB)
Figure 6A:
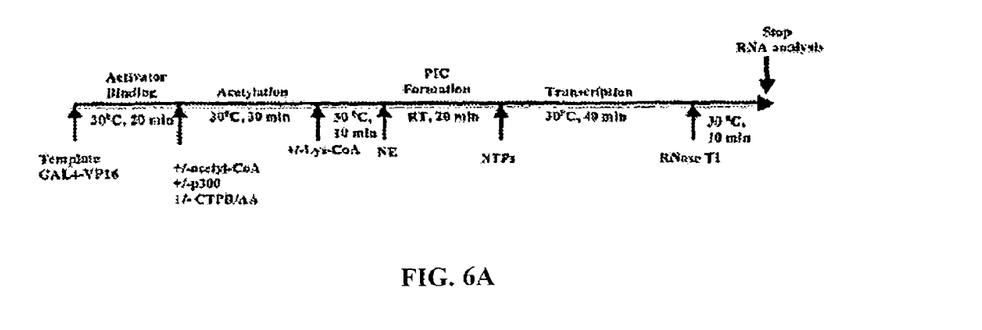
FIG. 6. Effect of increasing concentrations of CTPB and CTB on the HAT activity of p300.
Figure 6B:
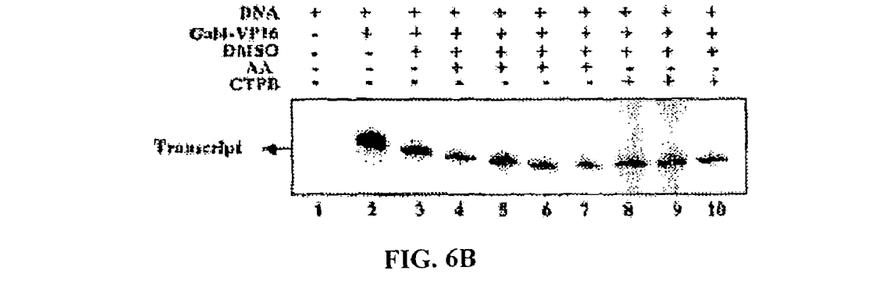
Figure 6C:
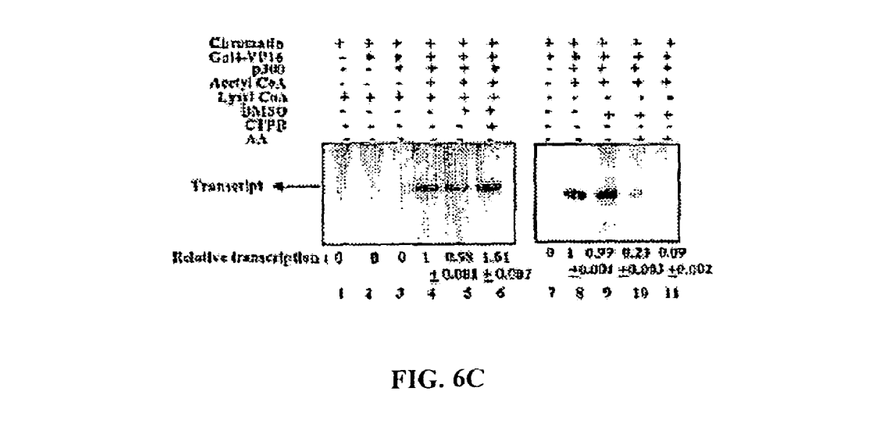
Figure 6D:
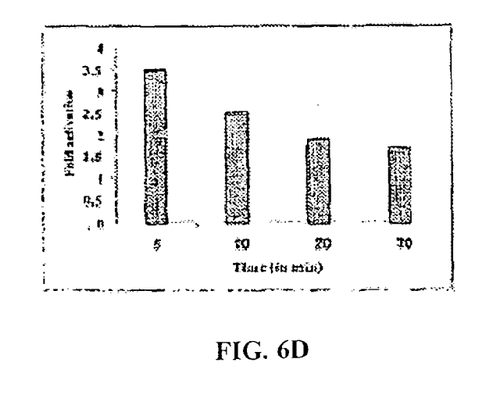
Figure 6E:
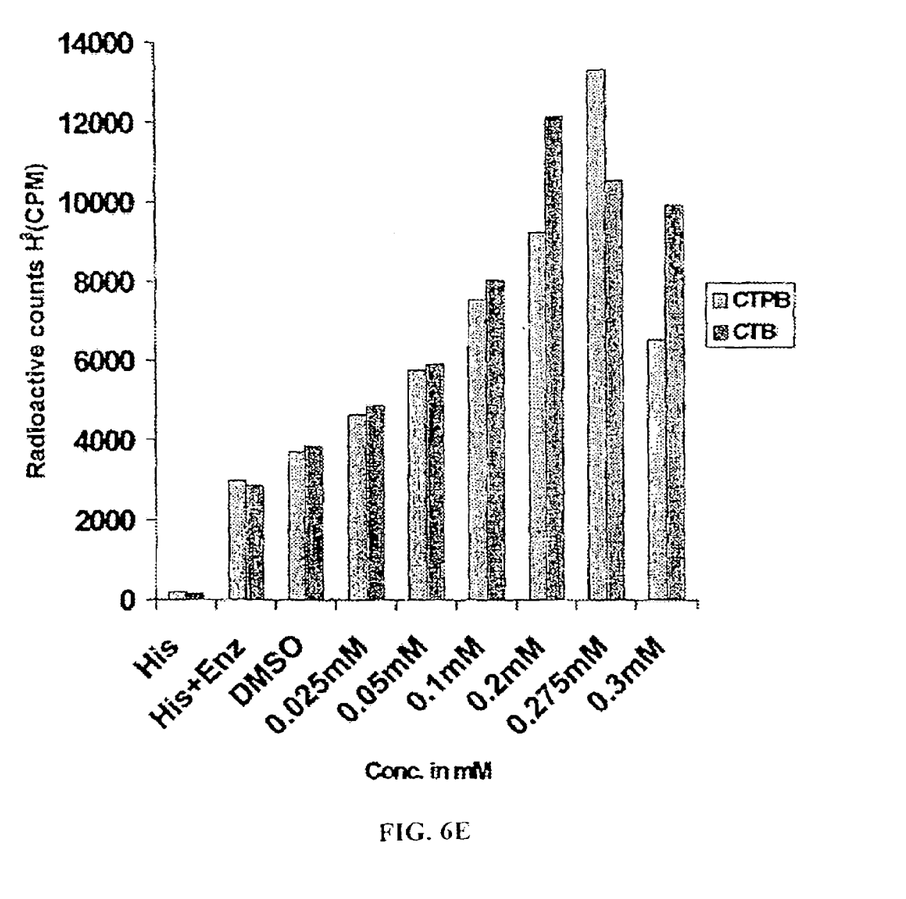
Figure 7:
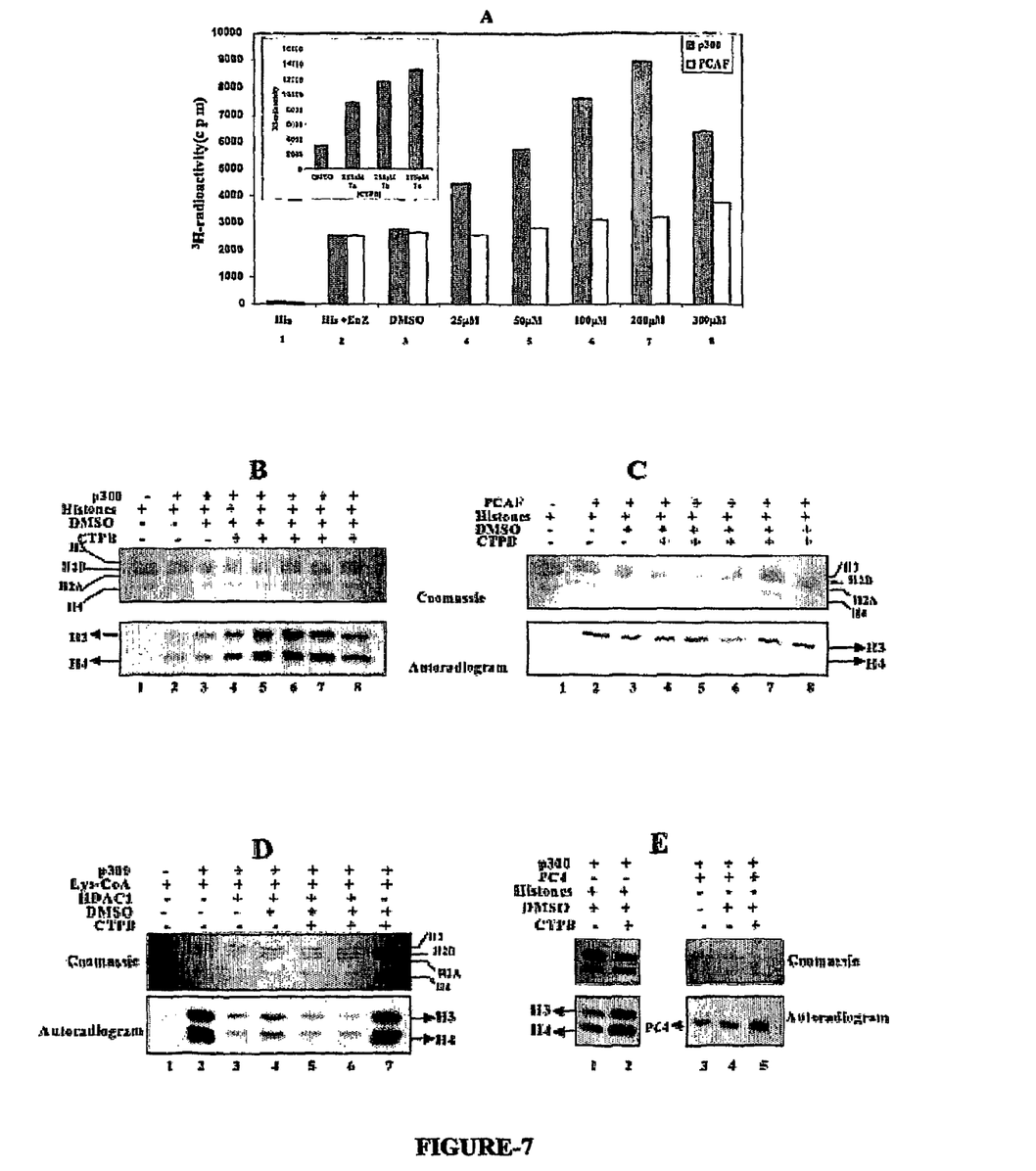
FIG. 7. Specificity of CTPB to activate the histone transferase activity of p300 and not that of PCAF.

Surprisingly, the amide derivatives (FIGS. 2 and 3) of the same compound show an enhancement of p300 HAT activity with human core histones (FIG. 4). These compounds are found to be specific for p300 since even at high concentration it cannot affect the HAT activity of PCAF (FIG. 5).

The inhibitor anacardic acid also inhibits p300 HAT activity dependent transcription from the chromatin template but not DNA transcription. These results indicate the HAT specific activity of anacardic acid. As expected, the amide derivatives enhance HAT-dependent chromatin transcription whereas transcription from the DNA template remained unaffected.

Most of the analogs of the amide compounds showed similar activity with regards to activation of histone acetylation, except one of the CN-derivatives, predominantly enhanced the acetylation of histone H3.

REFERENCES

1. Roth, S. Y., Denu, J. M., and Allis, C. D. (2001) *Annu. Rev. Biochem.* 70, 81-120
2. Sterner, D. E., and Berger, S. L. (2000) *Microbiol. Mol. Biol. Rev.* 64, 2, 435-459
3. Redner, R. L., Wang, J., and Liu, J. M. (1999) *Blood* 94, 2, 417-428
4. Marks, P. A., Rifkind, R. A., Richon, V. M., Breslow, R., Miller, T., and Kelly, W. K (2001) *Nat. Rev. Cancer* 1, 194-202
5. Giles, R. H., Peters, D. J., and Breuning, M. H. (1998) *Trends Genet.* 14, 178-183
6. Murata, T., Kurokawa, R., Krones, A., Tatsumi, K., Ishii, M., Taki, T., Masimo, M., Ohashi, H., Yanagisawa, M., Rosenfeld, M. G., Glass, C. K, and Hayashi Y. (2001) *Hum. Mol. Genet.* 10, 1071-1076
7. Ait-Si-Ali, S., Ramirez, S., Barre, F. X., Dkhissi, F., Magnaghi-Jaulin, L. Girault J. A., Robin, P., Knibiehler, M., Pritchard, L. L., Ducommun, B., Trouche, D., and Harel-Bellan, A. (1998) *Nature*, 396, 184-186
8. Kundu, T. K, Palhan, V., Wang, Z., An, W., Cole, P. A., and Roeder, R. G. (2000) *Mol. Cell* 6, 551-561
9. Cullis, P. M., Wolfeuden, R., Cousens, L., and Alberts, B. M. (1982) *J. Biol. Chem.* 257, 12165-12169
10. Lau, O. D., Kundu, T. K, Soccio, R. E., Ait-Si-Ali, S., Khalil, E. M., Vassilev, A., Wolfe, A. P., Nakatani, Y., Roeder, R. G., and Cole, P. A. (2000) *Mol. Cell* 589-595
11. Costanzo, A., Merlo, P., Pediconi, N., Fulco, M., Sartorelli, V., Cole, P. A., Fontemaggi, G., Fanciulli, M., Schiltz, L., Blandino, G., Balsano, C., and Levrero, M. (2002) *Mol. Cell* 9, 175-186
12. Kundu, T. K, Wang, Z., and Roeder, R. G. (1999) *Mol. Cell. Biol.* 19, 1605-1615
13. Wang, Z., and Roeder, R. G. (1997) *Genes Dev.* 11, 1315-1326
14. Prashandh Kumar, B. R., Swaminathan, V. Banerjee, S., and Kundu, T. K. (2001) *J. Biol. Chem.* 276, 16804-16809

The invention claimed is:
1. A compound of structural formula (I) for use as an activator of histone acetyltransferases:

wherein:
$R^1$ is selected from the group consisting of $C_3$- to $C_{16}$-alkyl and $C_3$- to $C_{16}$-alkene;
$R^2$ is selected from the group consisting of hydrogen, and $C_1$- to $C_6$-alkyl;
$R^3$ is selected from the group consisting of hydrogen, $C_1$- to $C_6$-alkyl, $CF_3$, $CCl_3$, $Cl_3$, F, Cl, I, and CN;
$R^4$ is selected from the group consisting of hydrogen, $C_1$ to $C_6$-alkyl, $CF_3$, $CCl_3$, $Cl_3$, F, Cl, I, and CN;
$R^5$ is selected from the group consisting of hydrogen, $C_1$- to $C_6$-alkyl, $CF_3$, $CCl_3$, $Cl_3$, F, Cl, I, and;
$R^6$ is selected from the group consisting of hydrogen, $C_1$- to $C_6$-alkyl, $CF_3$, $CCl_3$, $Cl_3$, F, Cl, I, and CN;
$R^7$ is selected from the group consisting of hydrogen, $C_1$- to $C_6$-alkyl, $CF_3$, $CCl_3$, $Cl_3$, F, Cl, I, and CN; and
$R^8$, $R^9$, and $R^{10}$ are independently selected from the group consisting of hydrogen, $C_1$- to $C_{16}$-alkyl, $C_1$- to $C_{16}$-alkene, and $C_1$- to $C_{16}$-alkoxy;
and salts thereof.

2. The compound of claim 1, wherein: $R^1$ is selected from the group consisting of n-propyl, isopropyl, n-butyl, t-butyl, $C_8H_{18}$, $C_{15}H_{26}$, $C_{15}H_{28}$, $C_{15}H_{30}$, and $C_{15}H_{32}$;
$R^2$ is selected from the group consisting of hydrogen, methyl, ethyl, n-propyl, isopropyl, n-butyl and t-butyl;
$R^3$ is selected from the group consisting of hydrogen, methyl, ethyl, n-propyl, isopropyl, n-butyl and t-butyl, $CF_3$, $CCl_3$, $Cl_3$, F, Cl, I, and CN;
$R^4$ is selected from the group consisting of hydrogen, methyl, ethyl, n-propyl, isopropyl, n-butyl and t-butyl, $CF_3$, $CCl_3$, $Cl_3$, F, Cl, I, and CN;
$R^5$ is selected from the group consisting of hydrogen, methyl, ethyl, n-propyl, isopropyl, n-butyl and t-butyl, $CF_3$, $CCl_3$, $Cl_3$, F, Cl, and CN;
$R^6$ is selected from the group consisting of hydrogen, methyl, ethyl, n-propyl, isopropyl, n-butyl and t-butyl, $CF_3$, $CCl_3$, $Cl_3$, F, Cl, I, and CN; and
$R^7$ is selected from the group consisting of H, methyl, ethyl, n-propyl, isopropyl, n-butyl and t-butyl, $CF_3$, $CCl_3$, $Cl_3$, F, Cl, I ,and CN.

3. A compound of structural formula (I):

wherein $R^1$, is selected from the group consisting of $C_{14}$- to $C_{16}$-alkyl and $C_{14}$- to $C_{16}$-alkenyl;
$R_2$ is selected from the group consisting of hydrogen, methyl, and ethyl;
$R^3$ is selected from the group consisting of hydrogen, $C_1$- to $C_6$-alkyl, $CF_3$, $CCl_3$, $Cl_3$, F, Cl, I,and CN;
$R^4$ is selected from the group consisting of hydrogen, $C_1$- to $C_6$-alkyl, $CF_3$, $CCl_3$, $Cl_3$, F, Cl, I, and CN;
$R^5$ is selected from the group consisting of hydrogen, $C_1$- to $C_6$-alkyl, $CF_3$, $CCl_3$, $Cl_3$, F, Cl, and I;
$R^6$ is selected from the group consisting of hydrogen, $C_1$- to $C_6$-alkyl, $CF_3$, $CCl_3$, $Cl_3$, F, Cl, I, and CN;
$R^7$ is selected from the group consisting of hydrogen, $C_1$- to $C_6$-alkyl, $CF_3$, $CCl_3$, $Cl_3$, F, Cl, I, and CN;
$R^8$ and $R^{10}$ are hydrogen; and
$R^9$ is selected from the group consisting of hydrogen and hydroxy; and salts thereof.

4. A compound of structural formula (I):

wherein $R^1$ is selected from the group consisting of $C_{12}$- to $C_{16}$-alkyl and $C_{12}$- to $C_{16}$-alkene:
$R^2$ is selected from the group consisting of hydrogen, and $C_1$- to $C_6$-alkyl;

$R^3$ is selected from the group consisting of hydrogen, $C_1$- to $C_6$-alkyl, $CF_3$, $CCl_3$, $CI_3$, F, Cl, I, and CN;

$R^4$ is selected from the group consisting of hydrogen, $C_1$- to $C_6$-alkyl, $CF_3$, $CCl_3$, $CI_3$, F, Cl, I, and CN;

$R^5$ is selected from the group consisting of hydrogen, $C_1$- to $C_6$-alkyl, $CF_3$, $CCl_3$, $CI_3$, F, Cl, and I;

$R^6$ is selected from the group consisting of hydrogen, $C_1$- to $C_6$-alkyl, $CF_3$, $CCl_3$, $CI_3$, F, Cl, I, and CN;

$R^7$ is selected from the group consisting of hydrogen, $C_1$- to $C_6$-alkyl, $CF_3$, $CCl_3$, $CI_3$, F, Cl, I, and CN; and $R^8$, $R^9$, and $R^{10}$ are independently selected from the group consisting of hydrogen, $C_1$- to $C_{16}$-alkyl, $C_1$- to $C_{16}$-alkene, and $C_1$- to $C_{16}$-alkoxy; and salts thereof.

5. A pharmaceutical composition for treating cancer, acquired immune deficiency syndrome (AIDS), HIV infection, and asthma, the composition comprising an anti-cancer-, anti-AIDS-, anti-HIV- or anti-asthma-effective amount of a compound of claim 1 or a pharmaceutically suitable salt thereof, in combination with a pharmaceutically suitable carrier.

* * * * *

UNITED STATES PATENT AND TRADEMARK OFFICE
CERTIFICATE OF CORRECTION

PATENT NO. : 7,332,629 B2  Page 1 of 1
APPLICATION NO. : 10/538328
DATED : February 19, 2008
INVENTOR(S) : Kundu et al.

It is certified that error appears in the above-identified patent and that said Letters Patent is hereby corrected as shown below:

IN THE SPECIFICATION:

Column 9:
Line 19, please delete "N2" and substitute therefor --M2--.

Column 13:
Line 57, please delete "4Chloro" and substitute therefor --4-Chloro--.

Column 14:
Line 8, please delete "4Cyano" and substitute therefor --4-Cyano--.
Line 27, please delete "4Chloro" and substitute therefor --4-Chloro--.

Column 15:
Line 21, please delete "N-4" and substitute therefor --N-(4--.

Column 18:
Line 9, please delete "(N+1)" and substitute therefor --(M+1)--.
Line 46, please delete "(CTPB)" and substitute therefor --(CTB)--.

IN THE CLAIMS:

Column 20:
Line 9, please delete "CN" and substitute therefor --I--.

Signed and Sealed this

Third Day of June, 2008

JON W. DUDAS
*Director of the United States Patent and Trademark Office*